United States Patent [19]
Anderson et al.

[11] 4,118,489
[45] Oct. 3, 1978

[54] INSECTICIDAL 2-(1-(HALOBENZOYL)-1-HYDROXYIMINOMETHYL)-5,6-DIHYDRO-4H-1,3-THIAZINES

[75] Inventors: Martin Anderson, Whitstable; Antony G. Brinnand, Sittingbourne, both of England

[73] Assignee: Shell Oil Company, Houston, Tex.

[21] Appl. No.: 856,701

[22] Filed: Dec. 2, 1977

Related U.S. Application Data

[63] Continuation-in-part of Ser. No. 779,646, Mar. 21, 1977, abandoned.

[30] Foreign Application Priority Data

Mar. 30, 1976 [GB] United Kingdom ............... 12745/76

[51] Int. Cl.$^2$ ..................... C07D 279/06; A01N 9/12
[52] U.S. Cl. ......................................... 424/246; 544/54
[58] Field of Search ........................... 544/54; 424/246

[56] References Cited

U.S. PATENT DOCUMENTS 4,022,775  5/1977  Roman et al. ...................... 544/54

Primary Examiner—John M. Ford

[57] ABSTRACT

Insecticidal 2-(1-(halobenzoyl-1-hydroxyiminomethyl)-5,6-dihydro-4H-1,3-thiazines.

3 Claims, No Drawings

INSECTICIDAL 2-(1-(HALOBENZOYL)-1-HYDROXYIMINOMETHYL)-5,6-DIHYDRO-4H-1,3-THIAZINES

This application is a continuation-in-part of application Ser. No. 779,646, filed Mar. 21, 1977 now abandoned.

DESRIPTION OF THE INVENTION

It has been found that interesting insecticidal and acaricidal properties are exhibited by oximes of the formula:

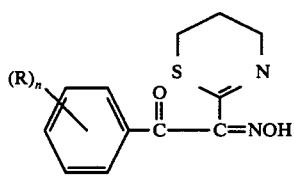

wherein $n$ is 1, 2 or 3, and R is chlorine or bromine, with the provisos that, relative to the carbon atom of the phenyl ring that is bonded to the carbonyl moiety, when $n = 1$, the moiety, R, is bonded at a carbon atom at the 3- or 4- position in the ring; when $n = 2$, the moieties, R, are bonded at the carbon atoms at the 2- and 4- or the 3- and 4- positions in the ring; when $n = 3$, the moieties, R, are bonded at the carbon atoms at the 2-, 3- and 4- positions in the ring.

These compounds are tautomers, the other tautomeric form being represented by the formula

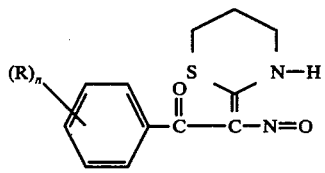

These oximes also can exist in the form of geometrical isomers - i.e., in the cis- and trans-configurations. As of the filing of this application, no individual isomer had been isolated, and no structure/insecticidal activity relationship study had been made. Under the circumstances, the invention comtemplates each of the insecticidally active isomers, as well as mixtures containing such isomers.

The oximes of this invention may be prepared by a process which comprises nitrosation of the corresponding enamines in the presence of an acid according to the equation:

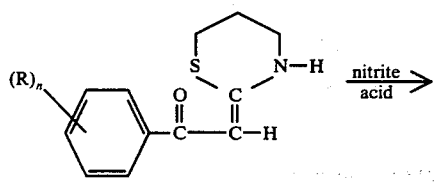

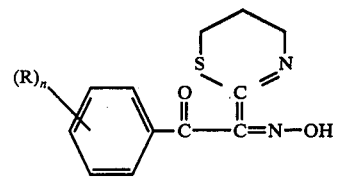

wherein $n$ and R have the meanings as specified hereinabove. The reaction can be suitably carried out by using acetic acid or a dilute mineral acid such as hydrochloric acid. Sodium nitrite can be suitably used but other nitrites normally applied in nitrosation reactions can be used as well. The reaction is conveniently carried out at moderate temperatures, preferably in the range of from 5° C. to 15° C. The (dilute) acid applied may also serve as the solvent. Also a mixture of solvents can be used.

The precursor enamines can be prepared by the following reaction sequence:

The appropriate haloacetophenone is mixed at a low temperature with carbon disulfide, methyl iodide, and sodium hydride in about the molar proportions: 1.0/1.5/3.0/2.0, in a solvent such as toluene, optionally slowly adding a small amount of dimethyl acetamide to the stirred cold mixture. The mixture then is poured over ice. The solid product is recovered by filtration and purified by recrystallization, for example, from methanol. The product can be represented by the formula:

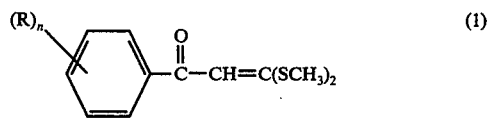

This method of preparation is described in Tetrahedron Letters, No. 43, pp. 4207–10 (1973).

The enamine is prepared by mixing 3-thiopropylamine hydrochloride and sodium carbonate in a small amount of water, adding the intermediate (1) in ethanol (molar proportions about 1/1/1), then removing solvent, adding water, extracting with chloroform, drying the extract, removing the solvent and recrystallizing the product from, for example, methanol, to giive the enamine,

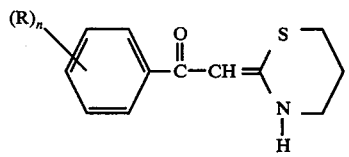

The oximes of the invention are of interest as insecticides. They show a promising activity against the Egyptian cotton leafworm (Spodoptera littoralis). The present invention therefore includes insecticidal compositons comprising a carrier and/or a surface active agent together with at least one oxime according to formula I. Likewise the present invention also includes a method of combatting insects at a locus which comprises applying to the locus an oxime of this invention or a composition containing at least one oxime of the invention.

The term "carrier" as used herein means a solid or fluid material, which may be inorganic or organic and of synthetic or natural origin, with which the active compound is mixed or formulated to facilitate its application to the plant, seed, soil or other object to be treated, or its storage, transport or handling.

The surface-active agent may be an emulsifying agent or a dispersing or a wetting agent; it may be non-ionic or ionic.

Any of the carrier materials or surface-active agents usually applied in formulating pesticides may be used in the compositions of the invention, and suitable examples of these are to be found, for example, in British Patent Specification No. 1,232,930.

The compositions of the invention may be formulated as wettable powders, dusts, granules, solutions, emulsifiable concentrates, emulsions, suspension concentrates or aerosols. Wettable powders are usually compounded to contain 25, 50 or 75% of toxicant and usually contain, in addition to solid carrier, 3–10%w of a dispersing agent and, where necessary, 0–10%w of stabilizer(s) and/or additives, such as penetrants or stickers.

Dusts are usually formulated as a dust concentrate having a similar composition to that of a wettable powder but without a dispersant, and are diluted in the field with further solid carrier to give a composition usually containing 0.5–10%w of toxicant. Granules are usually prepared to have a size between 10 and 100 BS mesh (1.676–0.152 mm), and may be manufactured by agglomeration or impregnation techniques. Generally, granules will contain 0.5–25%w toxicant and 0–10%w of additives such as stabilizers, slow release modifiers and binding agents. Emulsifiable concentrates usually contain, in addition to the solvent and, when necessary, co-solvent, 10–50% w/v toxicant, 2–20%w/v emulsifiers and 0–20%w/v of appropriate additives such as stabilizers, penetrants and corrosion inhibitors. Suspension concentrates are compounded so as to obtain a stable, non-sedimenting, flowable product and usually contain 10–75%w toxicant, 0.5–15%w of dispersing agents, 0.1–10%w of suspending agents such as protective colloids and thixotropic agents, 0–10%w of appropriate additives such as defoamers, corrosion inhibitors, stabilizers, penetrants and stickers, and as carrier, water or an organic liquid in which the toxicant is substantially insoluble; certain organic solids or inorganic salts may be dissolved in the carrier to assist in preventing sedimentation or as anti-freeze agents for water.

Aqueous dispersions and emulsions, for example compositions obtained by diluting a wettable powder or a concentrate according to the invention with water, also lie within the scope of the present invention. The said emulsions may be of the water-in-oil or of the oil-in-water type, and may have a thick "mayonnaise"-like consistency.

The compositions according to the invention may also contain other ingredients, for example, other compounds possessing pesticidal, especially insecticidal, acaricidal, herbicidal or fungicidal properties.

Preparation of individual species of the genus of Formula I is illustrated in the following examples. In each case, the identities of the products and of any precursors involved were confirmed by appropriate elemental and spectral analyses.

EXAMPLE 1

2-(1-(3,4-dichlorobenzoyl)-1-hydroxyiminomethyl)-5,6-dihydro-4H-1,3-thiazine (1)

32.81 g of 3,4-dichloroacetophenone, 9.60 g of sodium hydride, 22.8 g of carbon disulfide and 87.0 g of methyl iodide were mixed in toluene as solvent. 10 ml of dimethylacetamide was slowly added to the stirred mixture, which was held at about 20° C. during the addition. The mixture was stirred for 1 hour, then was warmed to 35° C. and stirred for 4 hours. About 150 g of ice was added to the mixture, then the mixture was filtered and the solid product was recrystallized from methanol to give 1A, m.p.: 160°–162° C.

24.7 g of 3-thiopropylamine hydrochloride, 21.2 g of sodium carbonate and a small amount of water were mixed and the mixture was stirred for 30 minutes. Then 58.6 g of 1A in ethanol was added and the stirred mixture was refluxed for 4 hours. The solvent was removed, water was added and the resulting mixture was extracted with chloroform. The extract was dried, the solvent was removed and the produce was recrystallized from methanol to give 1B, m.p.: 120°–122° C.

28.8 g of 1B was suspended in 250 ml of water. Sufficient dilute hydrochloric acid was added that the pH of the mixture was about 2.0. The suspension was cooled to 5°–10° C. and a solution of 13.8 g of sodium nitrite in 30 ml of water was added slowly to the stirred mixture, the temperature and pH being maintained at the indicated levels. The mixture was stirred for 2 hours. Dilute sodium hydroxide solution was added until the mixture pH was about 6.0, then an excess of sodium bicarbonate was added. Solid product was filtered and recrystallized from methanol to give 1, as a solid, m.p.: 178°–180° C.

EXAMPLES 2–6

Following procedures similar to those described in Example 1 (in some cases, using acetic acid, rather than hydrochloric acid), the following additional individual species of the genus of Formula I were prepared.

| Example No. | Compound No. | n | R | m.p. |
|---|---|---|---|---|
| 2 | 2 | 1 | 4-Cl | 153–154° C* |
| 3 | 3 | 2 | 2,4-Cl$_2$ | 108–111° C |
| 4 | 4 | 3 | 2,3,4-Cl$_3$ | 135–136° C |
| 5 | 5 | 1 | 3-Cl | 181–183° C |
| 6 | 6 | 1 | 4-Br | 173–174° C |

*with decomposition.

The insecticidal activity of compounds of the invention against the Egyptian cotton leafworm was tested as follows:

The compounds were formulated as solutions or suspensions in water containing 20% by weight of acetone and 0.05% by weight of Triton-X-100 as wetting agent. The formulations contained 0.4% by weight of the compounds to be tested. Pairs of leaves were removed from broad bean plants and placed on filter paper inside plastic petri-dishes. The leaves were sprayed using a spraying machine operated on the conveyor belt principle. The dosage was equivalent to 340 liters/hectare. After spraying the leaves were left for a drying period and then each leaf pair was infested with 10 larvae. Throughout the test the larvae were held under normal glasshouse conditions, fluctuating humidity and light. The number of dead and moribund insects was counted after 24 hours.

All of compounds 1 through 6 killed more than 80% of the insects.

We claim:

1. An oxime of the formula:

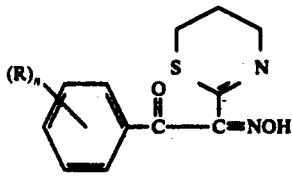 (I)

wherein n is 1, 2 or 3, and R is chlorine or bromine, with the provisos that, relative to the carbon atom of the phenyl ring that is bonded to the carbonyl moiety, when n = 1, the moiety, R, is bonded at a carbon atom at the 3- or 4- position in the ring; when n = 2, the moieties, R, are bonded at the carbon atoms at the 2- and 4- or the 3- and 4- positions in the ring; when n = 3, the moieties, R, are bonded at the carbon atoms at the 2-, 3- and 4- positions in the ring.

2. A method for killing insects of the genus *Spodoptera*, which comprises contacting said insects with an effective amount of a compound of claim 1.

3. An insecticidal composition which comprises a compound of claim 1 together with a carrier, optionally a surface-active agent.

* * * * *